United States Patent [19]
Gunaskera et al.

[11] Patent Number: 6,057,333
[45] Date of Patent: May 2, 2000

[54] DISCORHABDIN COMPOUNDS AND METHODS OF USE

[75] Inventors: Sarath P. Gunaskera; Peter J. McCarthy, both of Vero Beach; Shirley A. Pomponi; Amy E. Wright, both of Fort Pierce; Ross E. Longley, Vero Beach, all of Fla.

[73] Assignee: Harbor Branch Oceanographic Institution, Inc., Ft. Pierce, Fla.

[21] Appl. No.: 09/122,572

[22] Filed: Jul. 24, 1998

Related U.S. Application Data

[60] Provisional application No. 60/053,752, Jul. 25, 1997.

[51] Int. Cl.$^7$ .......................... A61K 31/44; C07D 401/14
[52] U.S. Cl. ........................... 514/278; 546/18; 424/573; 435/240.2
[58] Field of Search .............................. 514/278; 546/18; 424/573; 435/240.2

[56] References Cited

U.S. PATENT DOCUMENTS 4,731,366  3/1988  Munro et al. ........................... 514/278

OTHER PUBLICATIONS

Blunt, John W., Victoria L. Calder, Graham D. Fenwick, Robin J. Lake, John D. McCombs, Murray H.G. Munro, Nigel B. Perry (1987) "Reverse phase flash chromatography: a method for the rapid partitioning of natural product extracts" Journal of Natural Products 50(2):290–292.

Cheng, Jie–fei, Yasushi Ohizumi, Markus R. Walchli et al. (1988) "Prianosins B, C, and D, Novel Sulfur–Containing Alkaloids with Potent Antineoplastic Activity from the Okinawan Marine Sponge *Prianos melanos*" J. Org. Chem. 53:4621–4624.

Friedland, R.M., Robert H. Brown, Valeria Gagliardini, Joy Wang, Junying Yuan (1997) "Inhibition of ICE slows ALS in mice" Nature 388:31.

Hara, Hideaki et al. (1997) "Inhibition of interleukin 1β converting enzyme family proteases reduces ischemic and excitotoxic neuronal damage" Proc. Natl. Acad. Sci. USA 94:2007–2012.

Kerr, J.F.R., A.H. Wylllie, A.R. Currie (1972) "Apoptosis: A basic biological phenomenon with wide–ranging implications in tissue kinetics" Br. J. Cancer 26:239257.

Kim, Tae–Wan, Warren H. Pettingell, Yong–Keun Jung, Dora M. Kovacs, Rudolph E. Tanzi (1997) Science 277:373–376.

Kobayashi, J. et al. (1987) "Prianosin A, A Novel Antileukemic Alkaloid From The Okinawan Marine Sponge *Prianos melanos*" Tetrahedron Letters 28(42):4939–4942.

Milligan, C.E. et al. (1995) "Peptide Inhibitors of the ICE Protease Family Arrest Programmed Cell Death of Motoneurons in vivo and In Vitro" Neuron 15:385–393.

Munro, M. H. G. et al. (1987) Bioorganic Marine Chemistry, Scheuer, P. J. (ed.), Verlag Chemie: Heidelberg, vol. 1, Chapter 4, pp. 94–176.

Patel, Tushar, Gregory J. Gores, Scott H. Kaufmann 1996) "The role of proteases during apoptosis" FASEB 10:587–597.

Perry, Nigel B., John W. Blunt, John D. McCombs, Murray H.G. Munro (1986) "Discorhabdin C, a Highly Cytotoxic Pigment from a Sponge of the Genus Latrunculia" J. Org. Chem. 51:5476–5478.

Perry, Nigel B., John W. Blunt, Murray H. G. Munro (1988) "Cytotoxic Pigments From New Zealand Sponges Of The Genus Latrunculia: Discorhabdins A, B and C" Tetrahedron Letters 44(6):1727–1734.

Perry, Nigel B., John W. Blunt, Murray H.G. Munro (1988) "Discorhabdin D, an Antitumor Alkaloid from the Sponges *Latrunculia brevis* and *Prianos sp.*" J. Org. Chem. 53:4127–4128.

Schwartz, Lawrence M. and Carolanne E. Milligan (1996) "Cold thoughts of death: the role of ICE proteases in neuronal cell death" Trends in Neurosciences 19:555–562.

Sekine, Chiyoko et al. (1996) "Fas–Mediated Stimulation Induces IL–8 Secretion by Rheumatoid Arthritis Synoviocytes Independently of CPP32–Mediated Apoptosis" Biochem. Biophys. Res. Commun. 228:14–21.

Theriot, Julie A. and Lisa L. Satterwhite (1997) "New wrinkles in cytokinesis" Nature 385:388–389.

*Primary Examiner*—John Kight
*Assistant Examiner*—Charanjit S. Aulakh

*Attorney, Agent, or Firm*—Saliwanchik, Lloyd & Saliwanchik

[57] ABSTRACT

Discorhabdin compounds are derived from marine sponges of the genus Batzella or prepared by synthetic methods. These compounds, and pharmaceutical compositions containing them as active ingredients, are useful as immunomodulatory, antitumor agents, and/or caspase inhibitors.

5 Claims, 1 Drawing Sheet

Discorhabdin P (1)

(2)

(3)

6,057,333

DISCORHABDIN COMPOUNDS AND METHODS OF USE

CROSS-REFERENCE TO A RELATED APPLICATION

The subject application claims priority to provisional patent application Serial No. 60/053,752, filed Jul. 25, 1997.

FIELD OF THE INVENTION

This invention relates to discorhabdin compounds and compositions which have useful therapeutic properties. More particularly, the invention concerns discorhabdin compounds having antitumor and/or immunomodulatory activities, pharmaceutical compositions comprising such compounds, methods for the preparation of the compounds, and compositions and methods of their use.

BACKGROUND OF THE INVENTION

Immunomodulation is a developing segment of immunopharmacology. Immunomodulator compounds and compositions, as the name implies, are useful for modulating or regulating immunological functions in animals. Immunomodulators may be immunostimulants for building up immunities to, or initiate healing from, certain diseases and disorders. Conversely, immunomodulators may be immunoinhibitors or immunosuppressors for preventing undesirable immune reactions of the body to foreign materials, or to prevent or ameliorate autoimmune reactions or diseases.

Immunomodulators have been found to be useful for treating systemic autoimmune diseases, such as lupus erythematosus and diabetes, as well as immunodeficiency diseases. Further, immunomodulators may be useful for immunotherapy of cancer or to prevent rejections of foreign organs or other tissues in transplants, e.g., kidney, heart, or bone marrow.

Various immunomodulator compounds have been discovered, including FK506, muramylic acid dipeptide derivatives, levamisole, niridazole, oxysuran, flagyl, and others from the groups of interferons, interleukins, leukotrienes, corticosteroids, and cyclosporins. Many of these compounds have been found, however, to have undesirable side effects and/or high toxicity. New immunomodulator compounds are therefore needed to provide a wider range of immunomodulator function for specific areas with a minimum of undesirable side effects.

Various tumor and cancer related diseases afflict man and animals. The term tumor refers to abnormal masses of new tissue growth which is discordant with the economy of the tissue of origin or of the host's body as a whole. Tumors inflict mammals and man with a variety of disorders and conditions, including various forms of cancer. The seriousness of cancer is well known, e.g. cancer is second only to heart and vascular diseases as a cause of death in man. Tumors are common in a variety of mammals, and the prevention and control of the growth and regression of tumors in mammals is important to man.

Considerable research and resources have been devoted to oncology and antitumor measures, including chemotherapy. While certain methods and chemical compositions have been developed which aid in inhibiting, remitting, or controlling the growth of tumors and other forms of cancer, further antitumor methods and chemical compositions are needed.

It has been found that some natural products and organisms are potential sources for chemical molecules having useful biological activities. For example, the diterpene commonly known as taxol, isolated from several species of yew trees, is a mitotic spindle poison that stabilizes microtubules and inhibits their depolymerization to free tubulin (Fuchs, D. A., R. K. Johnson [1978] *Cancer Treat. Rep.* 62:1219–1222; Schiff, P. B., J. Fant, S. B. Horwitz [1979] *Nature* (London) 22:665–667). Taxol is also known to have antitumor activity and has undergone a number of clinical trials which have shown it to be effective in the treatment of a wide range of cancers (Rowinski, E. K. R. C. Donehower [1995] *N. Engl. J. Med.* 332:1004–1014). See also, e.g., U.S. Pat. Nos. 5,157,049; 4,960,790; and 4,206,221.

Marine life has been the source for the discovery of compounds having varied biological activities. Some of the United States patents which have issued for such inventions are as follows: U.S. Pat. No. 4,548,814 for didemnins, having antiviral activity, were isolated from a marine tunicate; U.S. Pat. No. 4,729,996 discloses compounds, having antitumor properties, that were isolated from marine sponges *Teichaxnella morchella* and *Ptilocaulis walpersi;* U.S. Pat. No. 4,808,590 discloses compounds, having antiviral, antitumor, and antifungal properties, isolated from the marine sponge Theonella sp.; and U.S. Pat. No. 4,737,510 discloses compounds, having antiviral and antibacterial properties, isolated from the Caribbean sponge *Agelas coniferin.* A number of publications have issued disclosing organic compounds derived from marine sponges, including Scheuer, P. J., Ed. (1978–1983) *Marine Natural Products, Chemical and Biological Perspectives,* Academic Press, New York; Faulkner, D. J. (1984) *Natural Products Reports* 1:551–598; Faulkner, D. J. (1986) *Natural Products Reports* 3:1–33; Faulkner, D. J. (1987) *Natural Products Reports* 4:539–576; Uemura, D., K. Takahashi, T. Yamamoto, C. Katayama, J. Tanaka, Y. Okumura, Y. Hirata (1985) *J. Am. Chem. Soc.* 107:4796–4798.

Discorhabdin compounds have been produced from marine sponges as disclosed in U.S. Pat. Nos. 4,731,366 and 4,874,767, and have been discussed in various publications including: Perry, N. B. et al (1986) *J Org. Chem.* 51:5476; Blunt, J. W. et al. (1987) *J Nat. Prod.* 50:290; Munro, M. H. G. et al. (1987) *Bioorganic Marine Chemistry,* Scheuer, P. J., Ed., Verlag Chemie: Heidelberg, Vol. 1, Chapter 4; Kobayashi, J. et al. (1987) *Tetrahedron Letters* 28:4939; Perry, N. B. et al (1988) *Tetrahedron Letters* 44:1727; Perry, N. B. et al. (1988) *J. Org. Chem.* 53:4127; and Cheng et al. (1988) *J. Org. Chem.* 53:4610.

The present invention, utilizing sponges as a source material, provides the art with new biologically active compounds and new pharmaceutical compositions useful as antitumor and immunomodulatory agents, as well as inhibitors of neurodegenerative processes. The present invention has added to the arsenal of pharmaceutical compounds by the discovery of novel compounds isolatable from extracts of marine sponges of the family Desmacididae.

BRIEF SUMMARY OF THE INVENTION

The subject invention provides discorhabdin compounds having advantageous biological activities. Specifically, in one embodiment, the discorhabdin compounds of the subject invention have been found to be useful in immune modulation and, more specifically, immune suppression. In a further embodiment, the compounds of the subject invention can be used to inhibit unwanted cellular proliferation. More particularly, the subject compounds, and compositions comprising the subject compounds, can be used for inhibiting in a human or animal the growth of tumor cells, including cells of breast, colon, CNS, or lung tumors, as well as human leukemia or melanoma cells. A further aspect of the subject invention pertains to the use of discorhabdin compounds as caspase inhibitors. In this context, the subject compounds can be used as inhibitors of neurodegeneration.

Also provided according to the subject invention are compositions containing the biologically active discorhabdin compounds, as well as methods for the preparation and use of the compounds and compositions.

The disclosure further provides methods for obtaining compounds of the invention. One method of producing the compounds useful according to the subject invention comprises the steps of collecting marine sponges of the genus Batzella, family Desmacididae and order Poecilosclerida, contacting such sponges with a selected organic solvent system, as described herein, to obtain an extract, fractionating the extract, and isolating discorhabdin P from the fractionated extract.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

DETAILED DISCLOSURE OF THE INVENTION

Figure 1:
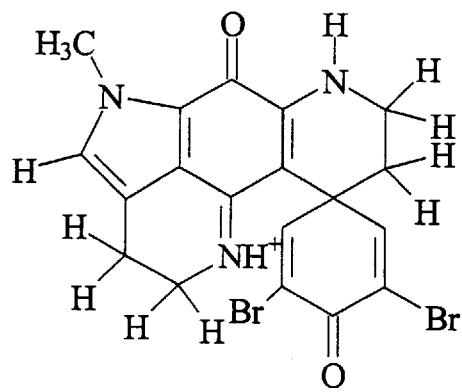
FIG. 1 shows an isolation scheme for discorhabdin P.
Figure 1:
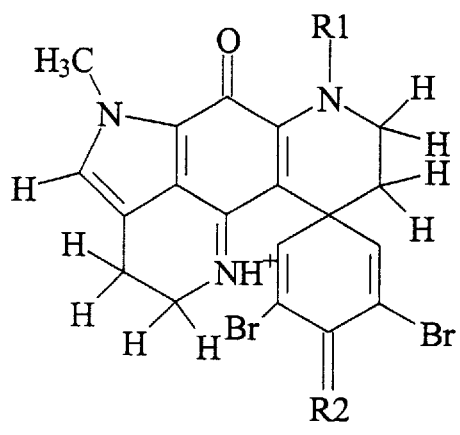
Figure 1:
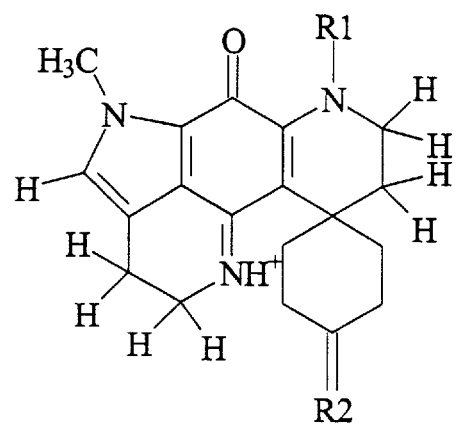

The subject invention pertains in part, to novel discorhabdin compounds and the use of these compounds as immunomodulators and/or antitumor agents. In a further embodiment the subject invention pertains to the use of discorhabdins as inhibitors of neurodegeneration.

In a specific embodiment, the subject invention pertains to a novel compound known as discorhabdin P, as well as its analogs and derivatives. As used in this application, the terms "analogs" and "derivatives" refer to compounds which are substantially the same as another compound but which may have been modified by, for example, adding side groups. Salts are also within the scope of the present invention. Analogs or derivatives of the exemplified compounds can be readily prepared using commonly known, standard reactions. These standard reactions include, but are not limited to, hydrogenation, methylation, acetylation, and acidification reactions.

The previously known discorhabdins (A→O), are a class of compounds which has an iminoquinone and a spiro-enone or spiro-dinone system, and are believed to be formed by the combination of a molecule of substituted tyrosine and a molecule of tryptamine. Discorhabdin P also possess the same iminoquinone and spirodienone system. However, discorhabdin P has a unique functionality, N-methylated pyrrole group which is lacking in all other related discorhabdins.

Discorhabdin P can be obtained from marine sponges of the genus Batiella. The sponge can be obtained, for example, from the western Great Bahama Bank, Bahamas (latitude 25° 15.562' N; longitude 79° 11.109' W). In one specific instance, the sample was obtained at a depth of 437 feet. Other aspects of the sponge collection are as follows: habitat, rubble slope; substrate, rock; morphology, 1–2 cm encrusting round patches, fistules scattered over surface; color, purple-brown; abundance, common.

Detailed Taxonomic Description

| | |
|---|---|
| Phylum | Porifera |
| Class | Demospongiae |
| Order | Poecilosclerida |
| Family | Desmacididae |
| Genus | Batzella |
| Species | undescribed |

The sponge has been assigned to the genus Batzelia, as described and discussed by Van Soest et al. (1966) pp. 95–97 (Bulletin de l'Institut Royal des Sciences Naturelles de Belgique, Biologie, 66 suppl:89–101). The sponge has a detachable ectosome and a spicule skeleton of strongyles of one size category. Some of the strongyles have malformed tips. The sponge incorporates sediment into its skeleton. There are numerous fistules scattered over the surface of the sponge. The sponge is purple-brown when alive, brown when preserved in ethanol. A taxonomic reference sample has been deposited in the Harbor Branch Oceanographic Museum, catalog number 003:00922.

Compounds useful according to the subject invention can be isolated by various fractionation and chromatographic techniques from the extracts obtained as disclosed herein. Preferred isolation procedures include various chromatography techniques, such as countercurrent chromatography, with suitable columns including multi-layer planetary coil columns. A variety of solvents are available for use as single or mixed eluents, such as tetrahydrofaran, methanol, ethyl acetate, acetonitrile, n-propanol, n-butanol, water, and equivalent solvents. Further purifications using such procedures may also be carried out on the recovered extractions. Preferred isolation techniques for further purifications include chromatographic operations such as high-pressure liquid chromatography (HPLC) with suitable columns and suitable solvents.

The subject invention pertains, in part, to compounds having the following structural formulas:

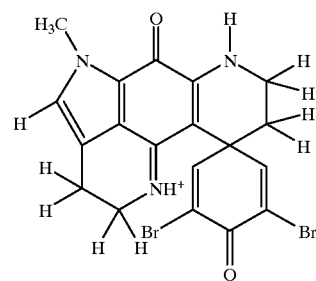

Discorhabdin P (1)

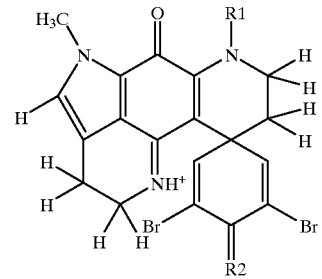

(2)

-continued

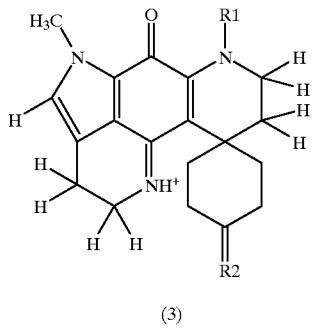

(3)

Included within the scope of the subject invention are salts, analogs and derivatives of Compounds 1, 2, and 3. The salts of the subject invention may be, for example, Cl⁻, Br⁻, $CH_3COO^-$, or $HSO_3O^-$. The analogs for Compounds 2 and 3 include lower alkylated products (R1 may be, for example, methyl, ethyl, or propyl; R2 can be O). Additional analogs of Compounds 2 and 3 include acylated products (R1=AcO, where A=phenyl or lower alkyls, R2 can be O). Further compounds of the subject invention include sodium borohydride or equivalent reaction products of Compound 1 (Compound 2, R1=H, R2=H, OH). Further compounds include Compound 1 catalytic hydrogenated products (Compound 3, R1=H, and R2=O).

In a specific example, the subject invention pertains to discorhabdin P, which has the following structure and characteristics:

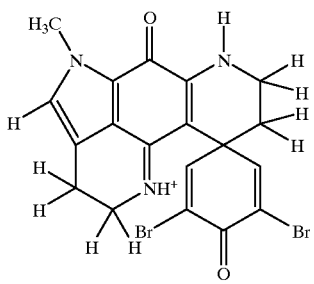

Discorhabdin P

18SG535 (same as 20SG431).

Orange colored crystals, Yield 0.015% of wet weight.

Melting Point >360° C.; crystals blackened at 162° C.

HRFABMS (M+H)⁺ appeared at 475.968, 477.968 and 479.968.

Molecular Formula $C_{19}H_{16}Br_2N_3O_2$ (Δ5 mmu).

UV (MeOH) λ max 488 (ε 3,090), 337 (10,100), 245 (19,900), 200 (18,450) nm.

IR (KBr) ν max 3385,3049,2930,2858,2363,1666,1653, 1569,1530,1438,1330, 1291,1023 and 696 cm⁻¹.

¹H NMR (500 MHZ, DMSO-d₆) δ 8.17 (2H, s), 7.45 (1H, s), 4.27 (3H,s), 4.18 (2H, t, J=7.8 Hz), 3.84 (2H, t, J=5.5 Hz), 2.91 (2H, t, J=7.8 Hz), 2.30 (2H, t, J=5.5Hz).

¹³C NMR (125.7 MHZ, DMSO-d₆) δ 172.4 (s), 170.0 (s), 157.3 (d), 157.3 (d), 153.7 (s), 143.2 (s), 129.0 (d), 121.5 (s), 118.4 (s), 121.5 (s), 118.4 (s), 116. 3 (s), 99.7 (s), 49.5 (t), 46.4 (s), 36.6 (t), 35.0 (q), 32.3 (t), 17.5 (t).

In one embodiment, the subject invention pertains to the immunosuppressive use of the subject discorhabdin compounds. These compounds can be used to reduce, suppress, inhibit, or prevent unwanted immune responses. Advantageously, this immunosuppressive can be achieved without cytotoxicity.

Thus, the compounds of the subject invention are useful for treatments of humans or animals requiring immunosuppressive. Examples of conditions for which immunosuppression is desired include, but are not limited to, treatment or prevention of autoimmune diseases such as diabetes, lupus, and rheumatoid arthritis. Immunosuppression is also frequently needed in conjunction with organ transplants. Immunosuppressive agents can also be utilized when a human or animal has been, or may be, exposed to superantigens or other factors known to cause overstimulation of the immune system. The compounds of the subject invention are also useful as standards to assess the activity of other putative immunosuppressive agents.

In a specific embodiment, the compounds of the subject invention have been found to inhibit calcineurin. Calcineurin is an enzyme and a member of the serine/threonine phosphatase family of cell signal transduction proteins. Calcineurin is recognized to be a principal signaling molecule that regulates immune responsiveness. Calcineurin's phosphatase activity is inhibited through an association with a complex formed by the immunosuppressant FK506 and an intracellular protein, FKBP-12 (FK506 Binding Protein), which results in immunosuppression. Therefore, inhibitors of calcineurin, such as the compounds of the subject invention, can be used to inhibit immune responsiveness through inhibition of calcineurin associated phosphatase activity. Inhibition of immune responsiveness by the subject compounds is useful for the treatment of conditions including systemic autoimmune disease, immunodeficiency diseases, immunotherapy of cancer or to prevent rejections of foreign organs or other tissues in transplants (i.e., kidney, heart, lungs, colon, liver, or bone marrow).

As described herein, the invention also comprises the use of the new compounds of the subject invention for inhibiting unwanted cellular proliferation and, in a preferred embodiment, for the inhibition of tumor growth. Thus, one aspect of the subject invention is a method for the antitumor treatment of a human in need of such treatment, i.e., a human hosting cancer cells, including breast, colon, or lung tumor cells, leukemia cells, CNS cancer cell lines, melanoma cell lines, ovarian cancer cell lines, renal cancer cell lines, and prostate cancer cell lines.

In accordance with the invention, methods for inhibiting tumors in a host comprise contacting tumor cells with an effective amount of the new pharmaceutical compositions of the invention. The tumor cells inhibited by the invention are those which are susceptible to the subject compounds described herein or compositions comprising those compounds.

A further aspect of the subject invention pertains to the use of the compounds of the subject invention as caspase inhibitors. Caspase inhibitors are useful in the treatment of a variety of chronic and acute inflammatory diseases such as pancreatitis, rheumatoid arthritis, osteoarthritis, asthma, inflammatory bowel disease, psoriasis and in certain neurological disorders such as Alzheimer's disease.

The caspases, which include CPP32, are a group of at least ten cysteine proteases (also known as interleukin-2 converting enzymes or $ICE_2$), which play a major role in the programmed cell death mechanism known as apoptosis (Patel, T., G. J. Gores, S. H. Kaufmann [1996] *FASEB* 10:587–597). These enzymes are the mamnmalian homologs of the ced-3 gene product that modulates apoptotic processes in the nematode *Caenorhabditis elegans*

(Schwartz, L. M., C. E. Milligan [1996] *Trends Neursci* 19:555–562). Mutations in ced-3 prevent apoptosis during normal development of the nematode and in mammals, inhibitors of caspase-3 (CPP32) have been shown to prevent apoptotic mediated death in a number of cell lines and in various tissues (Schwartz, L. M., C. E. Milligan [1996] *Trends Neursci* 19:555–562; Milligan, C. E., D. Prevette, H. Yaginuma, S. Homma, C. Cardwell, L. C. Fritz, K. J. Tomaselli, R. W. Oppenheim, L. M. Schwartz [1995] *Neuron* 15:385–393).

Apoptotic mechanisms play important roles in the normal development of the immune repertoire and in tissue remodeling during embryonic development in both vertebrates and invertebrates (Kerr, J. F. R., A. H. Wyllie, A. R. Currie [1972] *Br. J Cancer* 26:239–257). However, aberrant apoptosis has been implicated in a number of experimental and human disease states. For example, in acute CNS injury following hypoxic-ischemic insult in mice, there is evidence that caspase-induced apoptosis is the prime factor in neuronal destruction (Hara, H., R. M. Friedlander, V. Gagliardini, C. Ayata, K. Fink, Z. Huang, M. Shimizu-Sasamata, J. Yuan, M. A. Moskowitz [1997] *Proc. Natl. Acad. Sci. USA* 94:2007–2012). In addition, caspases have been implicated in chronic neurodegenerative disorders, which would suggest their role in the pathogenesis of amyotrophic lateral sclerosis (ALS) and in Alzheimer's disease (Friedlander, R. M., R. H. Brown, V. Gagliardini, J. Wang, J. Yuan [1997] *Nature* 388:31; Kim, T. -W., W. H. Pettingell,Y. -K. Jung, D. M. Kovacs, R. E. Tanzi [1997] *Science* 277:373–376). Caspase-3 (CPP32) has also been shown to be involved in the stimulation of IL-8 secretion of synoviocytes in rheumatoid arthritis which serves to increase joint inflammation and progress of the disease (Sekine, C., H. Yagita, T. Kobata, T. Hasunuma, K. Nishioka, K. Okumura [1996] *Biochem. Biophys. Res. Common.* 228:14–20). Therefore, inhibitors of caspase enzymatic activities may serve to prevent the pathological damage induced by caspase mediated apoptotic events.

A more complete understanding of the invention can be obtained by reference to preferred embodiments of the invention which are illustrated by the following specific examples of compounds, compositions, and methods of the invention. It will be apparent to those skilled in the art that the examples involve use of materials and reagents that are commercially available from known sources, e.g., chemical supply houses, so no details are given respecting them.

Following are examples which illustrate procedures for practicing the invention. These examples should not be construed as limiting. All percentages are by weight and all solvent mixture proportions are by volume unless otherwise noted.

EXAMPLE 1

Anti-Tumor Activity

P388 cells are obtained from Dr. J. Mayo, National Cancer Institute, Bethesda, Md., and A549 cells are obtained from American Type Culture Collection, Rockville, Md. All cell lines are maintained in Roswell Park Memorial Institute (RPMI) medium 1640 supplemented with 10% horse serum. All cell lines are cultured in plastic tissue culture flasks and kept in an incubator at 37° C. in humidified air containing 5% $CO_2$. Prior to testing, antibiotic-free stock cultures of each of the cell lines are subcultured to $10^6$ cells/ml by dilution in fresh growth medium at 2 to 3 day intervals.

To assess the antiproliferative effects of agents against the P388 cell line, 200 µl cultures (96-well tissue culture plates, Nunc, Denmark) are established at $1 \times 10^5$ cells/ml in drug-free medium or medium containing the test agent at 10.0, 1.0, 0.10 and 0.010 µg/ml. Solvent for all dilutions ethanol. All experimental cultures are initiated in medium containing Gentamycin sulfate (50 µg/ml; Schering Corporation, Kenilworth, N.J.). After 48 hr exposures, P388 cells are enumerated using 3-[4,5-Dimethylthiazol-2-yl]-2,5-diphenyltetrazolium bromide (MTT).

In the P388 assay, discorhabdin P was found to have an $IC_{50}$=0.025 µg/ml.

Similar procedures are utilized for A549 cells which require an additional 48 hr exposures prior to MTT addition. Results are expressed as percent inhibition compared to the negative (no drug) control. Positive drug controls are included to monitor drug sensitivity of each of the cell lines. These include varying dilutions of 5-fluorouracil, adriamycin, methotrexate and vinblastine.

To quantitate the effects on cell proliferation and resulting $IC_{50}$ values, 75 µl of warm growth media containing 5 mg/ml MTT is added to each well, cultures returned to the incubator, and left undisturbed for 90 minutes. To spectrophotometrically quantitate formation of reduced formazan, plates are centrifuged (900×g, 5 minutes), culture fluids removed by aspiration, and 200 µl of acidified isopropanol (2 ml concentrated HCl/liter isopropanol) added per well. The absorbance of the resulting solutions is measured at 570 nm with a plate reader (MR700 Microplate Reader, Dynatech, Laboratories, Chantilly, Va.). The absorbance of tests wells is divided by the absorbance of drug-free wells, and the concentration of agent that results in 50% of the absorbance of untreated cultures ($IC_{50}$) is determined by linear regression of logit-transformed data A linear relationship between tumor cell number and formazan production has been routinely observed over the range of cell densities observed in these experiments. The four standard drug controls are included in each assay as a check to monitor the drug sensitivity of each of the cell lines and $IC_{50}$ values are determined for each drug-cell combination.

In the A549 assay, discorhabdin P was found to have an $IC_{50}$=0.41 µg/ml.

EXAMPLE 2

Calcineurin Assay

Calmodulin was prepared from bovine brain according to the method of Wallace et al. ([1983] *Meth. Enzymol.* 102:39–47). The calmodulin was either used directly or coupled to sepharose-4B to form the calmodulin-sepharoseaffinity column necessary for the isolation of calcineurin. Calcineurin was prepared from bovine brain by the method of Tallant et al. ([1983] *Meth. Enzymol.* 102:244–286), concentrated, aliquoted and stored at −80° C.

Calcineurin activity was assayed in 96-well microtiter plates in a final volume of 50 µl. Each well contained 50 mM Tris-HCl pH 7.5, 0.5 mM $MnCl_2$, 0.05 mM $CaCl_2$, 1 mM DTT, 50 mM p-nitrophenylphosphate (pNPP), 0.3 µg calcineurin, a five-fold excess of calmodulin, and either test samples or control compounds. Plates were incubated at 30° C. for 60 min. Liberated p-nitrophenol was determined by the change in absorbance at 405 nm.

The activity of discorhabdin P in the calcineurin assay was found to be as follows:

Inhibition=64% at 5 µg/ml

Inhibition=33% at 0.5 µg/ml $IC_{50}$=0.55 µg/ml.

EXAMPLE 3

Caspase Inhibition

Test samples were aliquoted into 96 well microtiter plates and allowed to air dry. The stock CPP32 enzyme (kindly supplied by BASF, Worchester, Mass.) was diluted by adding 10 μl of the enzyme to 17 ml of reaction buffer (50 mM Hepes pH 7.5; 10% glycerol; 5 mM Dithiothreitol; 0.5 mM EDTA). A volume of 180 μl of the diluted enzyme was added to wells containing the dried test samples, or to empty wells (control). The contents of the microtiter wells were mixed by shaking on a plate shaker. Plates were incubated at 30 degrees C. for 5 minutes. A volume of 20 μL of substrate (Ac-DEVD-pNA) was added to each well which resulted in a final concentration of 25 μM. Controls for each plate consisted of an inhibitor control (50 nM DEVD-CHO final concentration); positive control (enzyme and substrate) and negative control (reaction buffer and substrate). The plates were covered with aluminum foil and mixed using a plate shaker for 5 minutes then incubated at 30 degrees C. for 30 minutes. Plates were read using on a plate reader with absorbance measured at 405 nM. Data was expressed as percent inhibition by comparing the absorbance values of test samples with those of the positive control (no sample). The $IC_{50}$ determination was defined as the concentration of sample/pure compound which resulted in a 50% inhibition of the enzyme-substrate absorbance value.

Compound 1 inhibited CPP32 with $IC_{50}$=0.37 μg/mL.

EXAMPLE 4

Uses, Formulations, and Administrations

Therapeutic and prophylactic application of the discorhabdin compounds, and compositions comprising them, can be accomplished by any suitable method and technique presently or prospectively known to those skilled in the art. Further, the compounds of the invention have use as starting materials or intermediates for the preparation of other useful compounds and compositions. The compounds of the invention are useful for various non-therapeutic and therapeutic purposes.

In one embodiment, compounds of the subject invention have effective immunomodulatory activity. Specifically, they are useful in regulating immune responses in animals and humans. Thus, pharmaceutical compositions containing compounds of the invention as active ingredients are useful in prophylactic or therapeutic treatment of an immunomodulatory response in humans or other mammals.

In one embodiment, the compounds of the subject invention can be used for immune reactions (in vivo/in vitro) that require modulation via T cell activity. Thus, one aspect of the subject invention concerns human in vivo suppression of T cell response, e.g., transplantation and autoimmunity.

The dosage administered will be dependent upon the immunomodulatory response desired; the type of host involved; its age, health, weight, kind of concurrent treatment, if any; frequency of treatment; therapeutic ratio and like considerations.

In one embodiment, the compounds of the subject invention are effective for inhibiting cell growth. Because of the antiproliferative properties of the compounds, they are useful to prevent unwanted cell growth in a wide variety of settings including in vitro uses. They are also useful as standards and for teaching demonstrations. They can also be used as ultraviolet screeners in the plastics industry since they effectively absorb UV rays. As disclosed herein, they are also useful prophylactically and therapeutically for treating cancer cells in animals and humans.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The compositions of the invention are advantageously used in a variety of forms, e.g., tablets, ointments, capsules, pills, powders, aerosols, granules, and oral solutions or suspensions and the like containing the indicated suitable quantities of the active ingredient. Such compositions are referred to herein and in the accompanying claims generically as "pharmaceutical compositions." Typically, they can be in unit dosage form, namely, in physically discrete units suitable as unitary dosages for human or animal subjects, each unit containing a predetermined quantity of active ingredient calculated to produce the desired therapeutic or prophylactic effect in association with one or more pharmaceutically acceptable other ingredients, e.g., diluent or carrier.

Where the pharmaceutical compositions are aerosols, the active ingredients can be packaged in pressurized aerosol containers with a propellant, e.g., carbon dioxide, nitrogen, propane, etc. with the usual adjuvants such as cosolvents, wetting agents, etc.

Where the pharmaceutical compositions are ointments, the active ingredient can be mixed with a diluent vehicle such as cocoa butter, viscous polyethylene glycols, hydrogenated oils, and such mixtures can be emulsified if desired.

It should be understood that the examples and embodiments described herein are for illustrative purposes only and that various modidfications or changes in light thereof will be suggested to persons skilled in the art and are to be included within the spirit and purview of this application and the scope of the appended claims.

We claim:

1. A method for inhibiting cancer cell proliferation wherein said method comprises administering to said cancer cells an effective amount of a discorhabdin compound, or an analog or salt thereof, wherein said discorhabdin compound, or analog or salt thereof has a structure selected from the group consisting of:

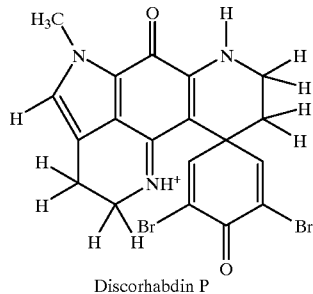

Discorhabdin P

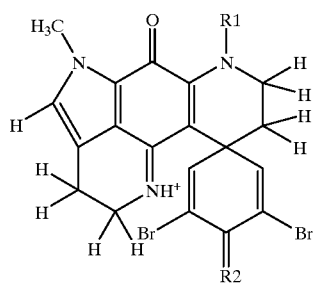

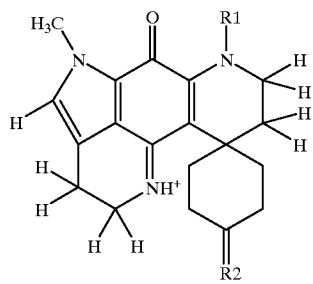

wherein
R1 is selected from the group consisting of H, methyl, ethyl, propyl, and AcO, and
R2 is selected from the group consisting of H, O, and OH.

2. The method, according to claim 1, wherein said cancer cells are selected from the group consisting of cancer cells of the breast, colon, central nervous system (CNS), lung, leukemia and melanoma.

3. The method, according to claim 1, wherein said discorhabdin compound is discorhabdin P, or a salt thereof.

4. A compound having a structure selected from the group consisting of:

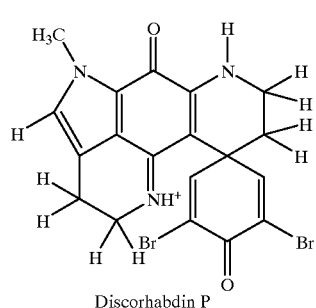

Discorhabdin P

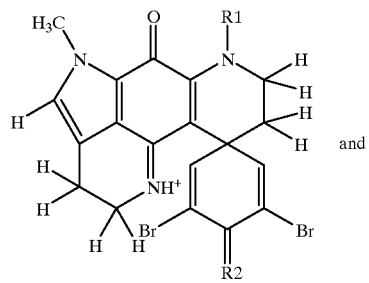

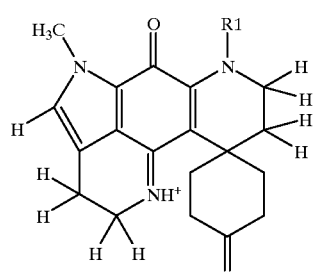

wherein
R1 is selected from the group consisting of H, methyl, ethyl, propyl, and AcO, and
R2 is selected from the group consisting of H, O, and OH.

5. The compound, according to claim 4, wherein said compound is discorhabdin P, or a salt thereof.

* * * * *

UNITED STATES PATENT AND TRADEMARK OFFICE
CERTIFICATE OF CORRECTION

PATENT NO. : 6,057,333

DATED : May 2, 2000

INVENTOR(S) : Gunasekera *et al.*

It is certified that error appears in the above-identified patent and that said Letters Patent is hereby corrected as shown below:

Cover Page: [75] Inventors: "Gunaskera" should read --Gunasekera--.

Column 2, line 20: "*Teichaxnella*" should read --*Teichaxinella*--.

Column 3, line 60: "Batiella" should read --*Batzella*--.

Column 4, line 11: "Batzelia" should read --*Batzella*--.

Column 4, line 31: "tetrahydrofaran" should read --tetrahydrofuran--.

Column 6, lines 5-6: "immunosuppresive" should read --Immunosuppression--.

Column 7, lines 35-36: "*Common.*" should read --*Commun.*--.

Column 8, line 33: "data A linear" should read --data. A linear--.

Signed and Sealed this

Third Day of April, 2001

*Attest:*

NICHOLAS P. GODICI

*Attesting Officer*    *Acting Director of the United States Patent and Trademark Office*